US006814711B1

(12) United States Patent
Voss et al.

(10) Patent No.: US 6,814,711 B1
(45) Date of Patent: Nov. 9, 2004

(54) INGROWN TOENAIL CURING KIT

(76) Inventors: Susan J. C. Voss, 10669 San Diego Mission Rd. #103, San Diego, CA (US) 92108; David J. Sauer, 10669 San Diego Mission Rd. #103, San Diego, CA (US) 92108

( * ) Notice: Subject to any disclaimer, the term of this patent is extended or adjusted under 35 U.S.C. 154(b) by 0 days.

(21) Appl. No.: 10/464,099

(22) Filed: Jun. 19, 2003

(51) Int. Cl.$^7$ .................................................. A61F 5/00
(52) U.S. Cl. ......................................... 602/30; 128/893
(58) Field of Search ..................... 602/23, 30; 128/888, 128/893, 894

(56) References Cited

U.S. PATENT DOCUMENTS

| | | |
|---|---|---|
| 2,505,086 A | 4/1950 | Andrews |
| 4,057,055 A | 11/1977 | Clark |
| 4,559,957 A * | 12/1985 | Hokama ...................... 132/73 |
| 4,674,486 A | 6/1987 | Hoffman |
| 4,860,736 A * | 8/1989 | Kaitz .......................... 128/155 |
| 5,261,872 A | 11/1993 | Goldenberg |
| 5,370,140 A | 12/1994 | Meyerovich |
| 5,862,811 A * | 1/1999 | Steele ......................... 132/200 |
| 6,095,995 A | 8/2000 | Machida |

* cited by examiner

*Primary Examiner*—Michael Anthony Brown

(57) ABSTRACT

An ingrown toenail curing kit includes a resiliently compressible material. A liquid adhesive is positioned in a container. An elongated implement has a first end and a second end. The material may be positioned under a toenail with the elongated implement. The material may be secured under the toenail with the adhesive until the toenail has properly grown out.

6 Claims, 2 Drawing Sheets

INGROWN TOENAIL CURING KIT

BACKGROUND OF THE INVENTION

1. Field of the Invention

The present invention relates to ingrown toenail curing devices and more particularly pertains to a new ingrown toenail curing device for providing the articles needed to prevent and cure ingrown toenails.

2. Description of the Prior Art

The use of ingrown toenail curing devices is known in the prior art. U.S. Pat. No. 4,674,486 describes a device that includes a plurality of strips attached to the top of the toenail for lifting the edges of the toenail. Another type of ingrown toenail curing device is U.S. Pat. No. 5,261,872 that includes a single strap that is attached to the top of the toenail for lifting the edges of the toenail.

While these devices fulfill their respective, particular objectives and requirements, the need remains for a device that includes all of the articles for inserting material underneath the toenail.

SUMMARY OF THE INVENTION

The present invention meets the needs presented above by providing a resiliently compressible material. A liquid adhesive is positioned in a container. An elongated implement has a first end and a second end. The material may be positioned under a toenail with the elongated implement. The material may be secured under the toenail with the adhesive until the toenail has properly grown out.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
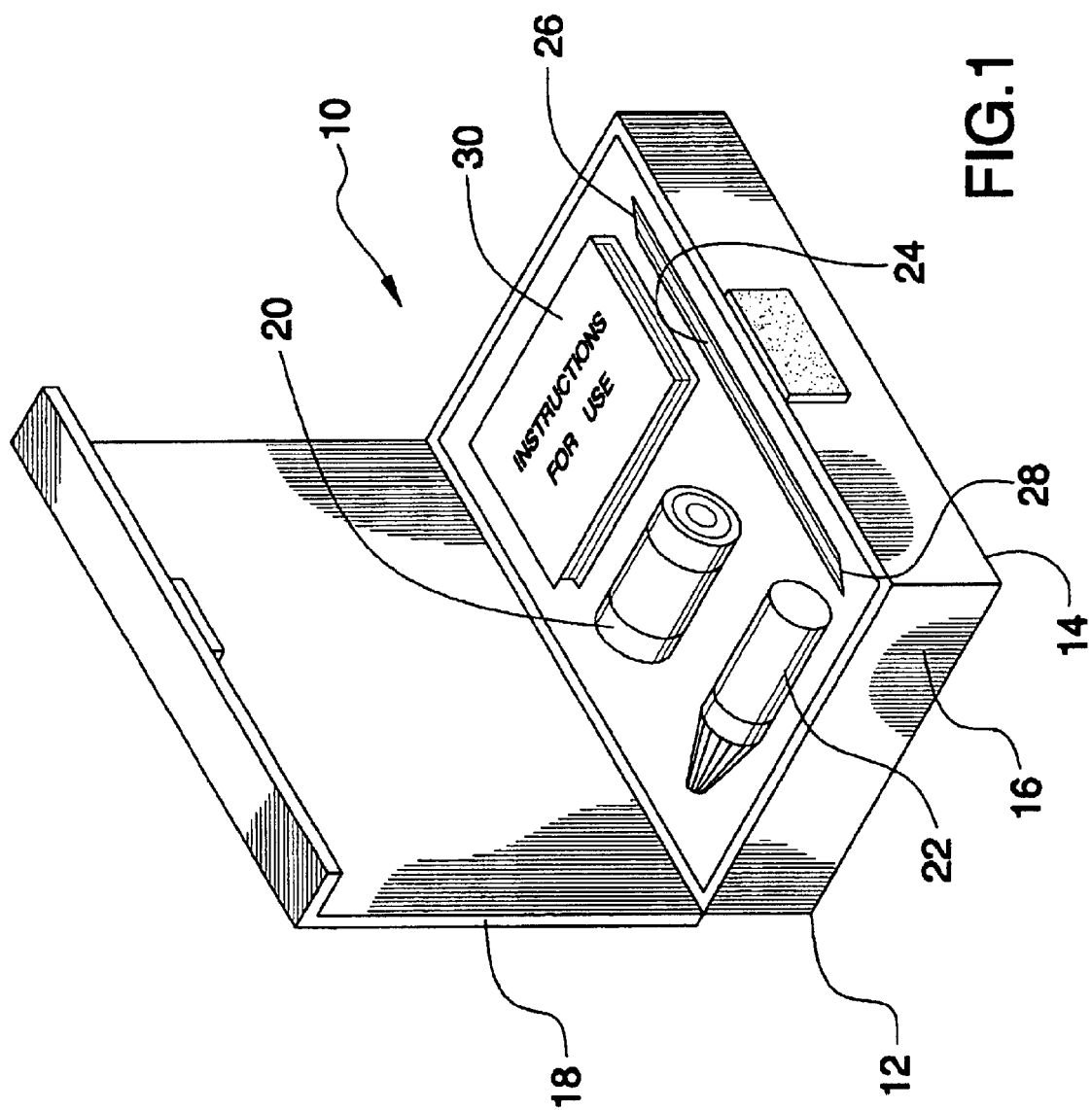
FIG. 1 is a schematic perspective view of a ingrown toenail curing kit according to the present invention.
Figure 2:
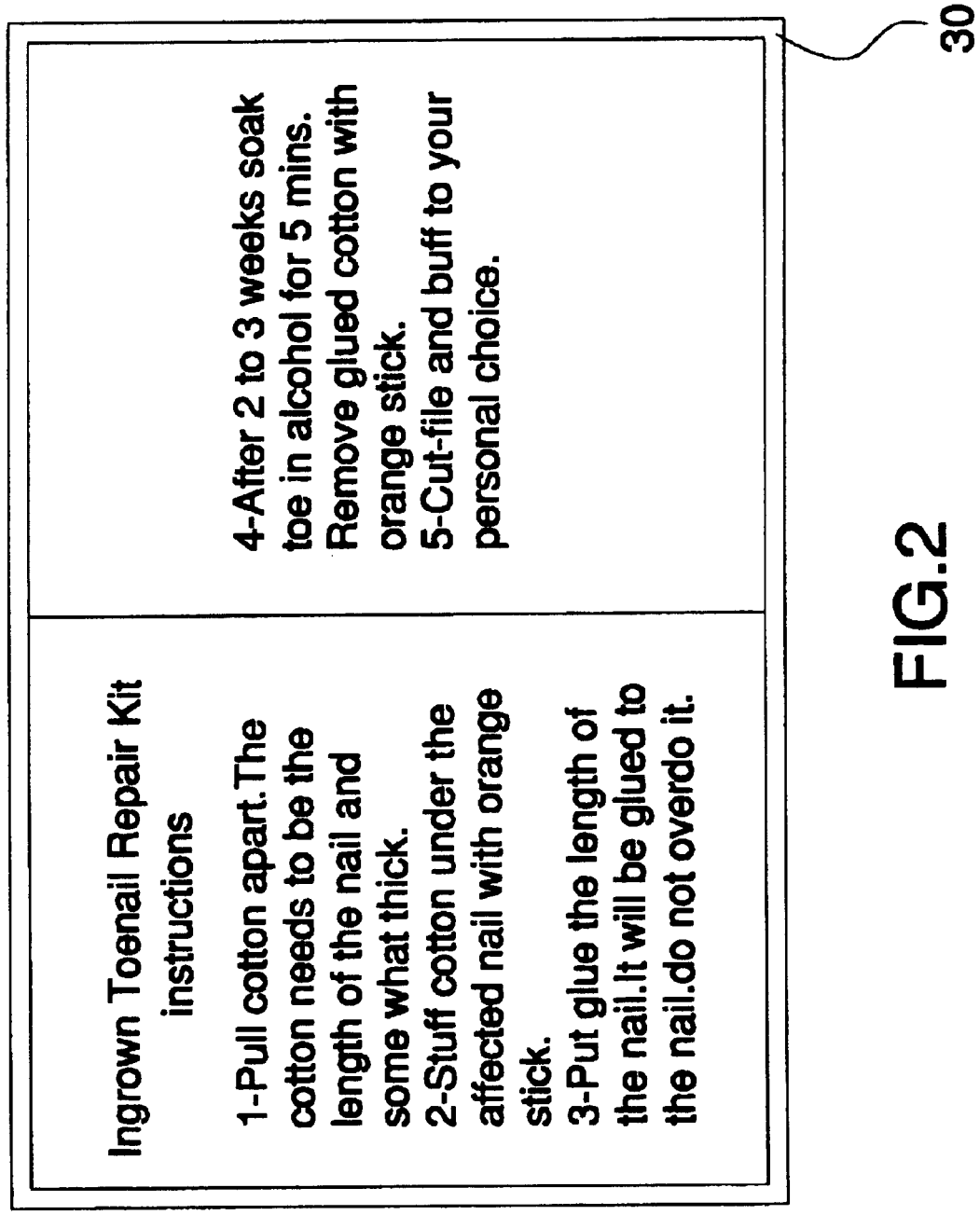
FIG. 2 is an instruction pamphlet for use of the present invention.

With reference now to the drawings, and in particular to FIGS. 1 and 2 thereof, a new ingrown toenail curing device embodying the principles and concepts of the present invention and generally designated by the reference numeral 10 will be described.

As best illustrated in FIGS. 1 and 2, the ingrown toenail curing kit 10 generally comprises a housing 12 having a bottom wall 14 and a peripheral wall 16 that is attached to and extends upwardly from the bottom wall. A cover 18 is pivotally coupled to the peripheral wall 16 for selectively opening or closing the housing 12. The housing 12 may alternatively include, but is not limited to, shrink wrap, a cardboard box either with our without plastic wrap, a metallic box, or a cloth bag.

A resiliently compressible material 20 is removably positioned in the housing 12. The material 20 preferably comprises a cotton material that is supplied in a roll such that strips of the cotton material may be removed from the roll. The cotton also include cotton squares or strips of cotton, woven cotton strands and cotton balls. The material 20 would be a sanitized material.

A liquid adhesive is supplied within a container 22. The container 22 is removably positioned in the housing. The liquid adhesive is ideally an acrylic glue used conventionally as nail glue for adhering tips to nails.

An elongated implement 24 is provided that has a tapered first end 26 a tapered second end 28. The elongated implement 24 preferably comprises an orangewood stick of the type conventionally used in manicuring. Orangewood is preferred due to its ability to retain its rigidity and not splinter when wet.

Preferably, an instruction pamphlet 30 is included with the kit 10 and positioned in the housing 12.

In use, the material is stuffed under a toenail with the elongated implement. The material is cut so that it is the length of the toenail. The material is formed in a roll before positioning below the toenail and has a length generally equal to the toenail. The adhesive is positioned along a length of the toenail and over the material to hold the material in place. Once the toenail has grown out properly, the toe is soaked in alcohol or other agent depending on the type of glue used until the cotton is released from the toenail. The elongated implement may be used for aiding in the removal of the material.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method of curing an ingrown toenail comprising the steps of:

providing a housing;

providing a resiliently compressible material;

providing a liquid adhesive, said liquid adhesive being positioned in a container;

providing an elongated implement having a first end and a second end;

removably positioning each of said material, said container and said elongated implement into said housing;

cutting said material to a length equal to a length of the toenail;

rolling said material so that a roll of material is defined;

stuffing said roll of material under the toenail with said elongated implement; and applying said adhesive along the toenail and over said roll of material so that said roll of material is secured under the toenail until the toenail is healed.

2. The method according to claim 1, wherein said housing has a bottom wall and a peripheral wall being attached to and extending upwardly from said bottom wall, a cover being pivotally coupled to said peripheral wall for selectively opening or closing said housing.

3. The method according to claim 1, wherein said material comprises a cotton material.

4. The method according to claim 1, wherein said first and second ends of said elongated implement are tapered.

5. The method according to claim 1, wherein said elongated implement comprises an orangewood stick.

6. A method of curing an ingrown toenail comprising the steps of:

providing a housing having a bottom wall and a peripheral wall being attached to and extending upwardly from said bottom wall, a cover being pivotally coupled to said peripheral wall for selectively opening or closing said housing;

providing a resiliently compressible material, said material comprising a cotton material;

providing a liquid adhesive, said liquid adhesive being positioned in a container;

providing an elongated implement having a first end and a second end, said first and second ends being tapered, said elongated implement comprising an orangewood stick;

removably positioning each of said material, said container and said elongated implement into said housing;

cutting said material to a length equal to a length of the toenail;

rolling said material so that a roll of material is defined;

stuffing said roll of material under the toenail with said elongated implement; and applying said adhesive along the toenail and over said roll of material so that said roll of material is secured under the toenail until the toenail is healed.

\* \* \* \* \*